United States Patent [19]

Bennett et al.

[11] Patent Number: 5,134,997
[45] Date of Patent: Aug. 4, 1992

[54] RATE RESPONSIVE PACEMAKER AND PACING METHOD

[75] Inventors: Tommy D. Bennett, Shoreview; Lucy M. Nichols, Maple Grove; Glenn M. Roline, Anoka; David L. Thompson, Fridley, all of Minn.

[73] Assignee: Medtronic, Inc., Minneapolis, Minn.

[21] Appl. No.: 567,204

[22] Filed: Aug. 14, 1990

[51] Int. Cl.⁵ ........................... A61N 1/362
[52] U.S. Cl. ........................... 128/419 PG
[58] Field of Search ................. 128/419 PG

[56] References Cited

U.S. PATENT DOCUMENTS

| | | | |
|---|---|---|---|
| 4,428,378 | 1/1984 | Anderson et al. | 128/419 PG |
| 4,535,774 | 8/1985 | Olson | 128/419 PG |
| 4,688,573 | 8/1987 | Alt | 128/419 PG |
| 4,803,987 | 2/1989 | Calfee et al. | 128/419 PG |
| 4,884,576 | 12/1989 | Alt | 128/419 PG |
| 4,966,146 | 10/1990 | Webb et al. | 128/419 PG |

*Primary Examiner*—William E. Kamm
*Assistant Examiner*—Kennedy J. Schaetzle
*Attorney, Agent, or Firm*—John A. Rissman; Harold R. Patton

[57] ABSTRACT

A rate responsive pacemaker and a pacing method for optimizing the pacing decay curve after a period of increased activity. The pacing method includes the steps of selecting a set of predetermined achievement criteria such as an achievement rate and an achievement time interval. The achievement rate is selected between an upper pacing rate and a first pacing switch rate threshold. The pacing method then determines whether the achievement criterion has been met. If the achievement criterion has been met, then the decay time constant of the decay curve changes from a first value to a second value, as the pacing rate drops below the first pacing switch rate threshold. A second pacing switch rate threshold lower than the first pacing switch rate threshold is then selected, and, if the achievement criteria have been met, then the decay time constant of the decay curve is modified from the second value to a third value, as the pacing rate drops below the second pacing switch rate threshold.

16 Claims, 5 Drawing Sheets

RATE RESPONSIVE PACEMAKER AND PACING METHOD

BACKGROUND OF THE INVENTION

1. Field of the Invention

The present invention generally relates to medical cardiac pacers, and more particularly, it relates to a pacer of the type which responds to the patient's metabolic demand and varies the decay rates in substantial similarity to the heart's normal behavior.

2. Description of the Prior Art

Early cardiac pacemakers provided a fixed-rate stimulation pulse generator that could be reset, on demand, by sensed atrial and/or ventricular depolarizations. Modern pacemakers include complex simulation pulse generators, sense amplifiers and leads which can be configured or programmed to operate in single or dual chamber modes of operation, delivering pacing stimuli to the atrium and/or ventricle at fixed rates or rates that vary between an upper rate limit and a lower rate limit.

In recent years, single and dual chamber pacemakers have been developed which measure parameters which are directly or indirectly related to metabolic requirements (e.g., demand oxygenated blood) and vary the pacing rate in response to such parameters. Such measured parameters include, for example, physical activity of the body, right ventricular blood pressure and the change of right ventricular blood pressure over time, venous blood temperature, venous blood oxygen satuation, respiration, minute ventilation, and various pre and post-systolic time intervals measured by impedance or pressure sensing within the right ventricle of the heart. Such sensor-driven pacemakers have been developed for the purpose of restoring rate response to exercise in patients lacking the ability to increase rate adequately by exertion.

In general, a rate responsive pacemaker includes a sensor which produces an output that varies between a maximum sensor output level and a minimum sensor output level ("Sensor Output"), and a packing rate is provided by the pacemaker ("Pacing Rate") which typically varies as a linear or monotonic function ("f") of the sensor output, between a selectable lower pacing rate ("Lower Rate") and upper pacing rate ("Upper Rate"). Function f has a selectable slope (i.e., Pacing Rate change/Sensor Output Change) adjustable by means of an external programmer in conjunction with the Lower and Upper Rates. Thus, the Pacing Rate typically provided is equal to the pre-selected Lower Rate plus an increment which is a function of the measured Sensor Output, as follows:

Pacing Rate=Lower Rate+$f$(Sensor Output).

While this rate response technique provides a useful and workable system between the programmed parameters, the behavior of the pacemaker is complex and not often readily apprehended. Among these rate responsive pacemakers, those that measure the physical activity of the patient by means of a piezoelectric transducer have become popular among the various rate responsive pacemakers. Such an activity rate responsive pacemaker is described in U.S. Pat. No. 4,485,813 issued to Anderson et al.

Some temperature sensing pacemakers have employed relatively more complex functions to take into account the initial dip in temperature due to the onset of exercise. One such pacemaker is described in U.S. Pat. No. 4,719,920 issued to Alt.

Furthermore, the decay slope of conventional pacemakers do not approximate the heart's normal behavior, in that they are programmed to follow a curve based on a single time constant. This discrepancy between the normal heart deceleration function at the end of physiologic stresses, such as physical activity, and the conventional decay function has not been totally rectified by any pacemaker presently available on the market.

Wherefore, it is desirable to have a new cardiac pacemaker and method of pacing with activity or other rate responsive dependent parameters, for responding to the patient's metabolic demand and for varying the attack and decay pacing rates in harmony with the heart's normal behavior.

BRIEF SUMMARY OF THE INVENTION

It is therefore one object of the present invention to address the above problems and to provide adequate solutions thereto.

Briefly, the above and further objects and features of the present invention are realized by providing a rate responsive pacemakers and a pacing method for optimizing the pacing decay curve after a period of increased activity. The pacing method includes the steps of selecting a set of predetermined achievement criteria such as an achievement rate and an achievement duration or time interval.

The achievement rate is initially selected between an upper pacing rate and a first pacing switch rate threshold. The pacing method then determines whether the achievement criterion has been met. If the achievement criterion has been met, then the decay time constant of the decay curve changes from a first value to a second value, as the pacing rate drops below the first pacing switch rate threshold.

A second pacing switch rate threshold lower than the first pacing switch rate threshold is then selected, and, if the achievement criterion has been met, then the decay time constant of the decay curve is modified from the second value to a third value, as the pacing rate drops below the second pacing switch rate threshold. The second value of the time constant for the decay curve should be longer than the value, in order to allow a slower decay of the pacing rate. In the preferred embodiment, the third value of the time constant for the decay curve is made substantially equal to the first value.

If on the other hand the achievement criteria have not been met, then the time constant of the decay curve is not modified.

The cardiac pacemaker also periodically calculates the new activity pacing rate, and then calculates the new activity target rate based upon the activity sensor output. In the preferred embodiment, the achievement rate is calculated as follows:

Achievement Rate=Lower Rate+$a$ (Upper Rate−Lower Rate), 10 where "a" is a percentile value.

The first or upper pacing switch rate threshold is calculated as follows:

First Pacing Switch Rate=Lower Rate+$u$ (Upper Rate−Lower Rate), where "u" is a percentile value.

The second or lower pacing switch rate threshold is calculated as follows:

Second Pacing Switch Rate = Lower Rate + 10% Lower Rate.

The target rate is calculated according to the following equation:

$$TR = \frac{(\text{Activity Count} + D)}{C} * (32768 * 60/328).$$

In the above equations a, u, C, D, Lower Rate and Upper Rate are selectively programmable values.

By using the above inventive pacing method, the pacemaker responds to the patient's metabolic demand and varies the decay rates in harmony with the heart's normal behavior, and allows for a gradual decrement in the pacing rate during the decay or deceleration period.

BRIEF DESCRIPTION OF THE DRAWINGS

The above and other objects and features of the present invention and the manner of attaining them, will become apparent, and the invention itself will be best understood, by reference to the following description and the accompanying drawings, wherein.

DESCRIPTION OF THE PREFERRED EMBODIMENT

Figure 1:
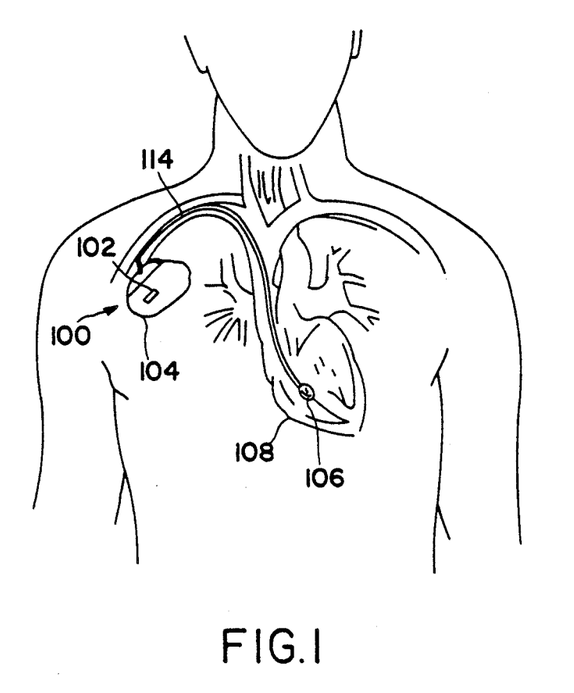
FIG. 1 graphically illustrates a multi-sensor pacemaker employing the present invention.

Referring now to the drawings and more particularly to FIG. 1 thereof, there is illustrated a multi-sensor pacemaker 100 according to the present invention. The preferred embodiment of the pacemaker 100 includes two sensors, and activity sensor 102 secured to a can or housing 104, and a pressure sensor 106 implanted within the patient's heart 108.

The operation of the sensors 102 and 106 is described in greater detail in two co-pending U.S. patent applications Ser. No. 07/567,476, entitled "OPTIMIZATION FOR RATE RESPONSE CARDIAC PACEMAKER", and Ser. No. 07/567,882, entitled "RATE RESPONSIVE PACEMAKER AND METHODS FOR OPTIMIZING ITS OPERATION", both filed on even date herewith and are incorporated herein by reference. It should be understood that the present invention is not limited to a dual sensor pacemaker, and that other sensors beside activity and pressure sensors could also be used according to the present invention. Nor is the present invention limited to a single chamber pacemaker. A multi-chamber (i.e. dual chamber pacemaker) can also be used in conjunction with the present invention. It should also be understood that while the present invention will be described in relation to the decay curve within the context of an activity-based rate responsive pacemaker, the inventive concept can be extrapolated for the attack curve, as well as for use in pressure or multi-sensor pacemaker.

Figure 2:
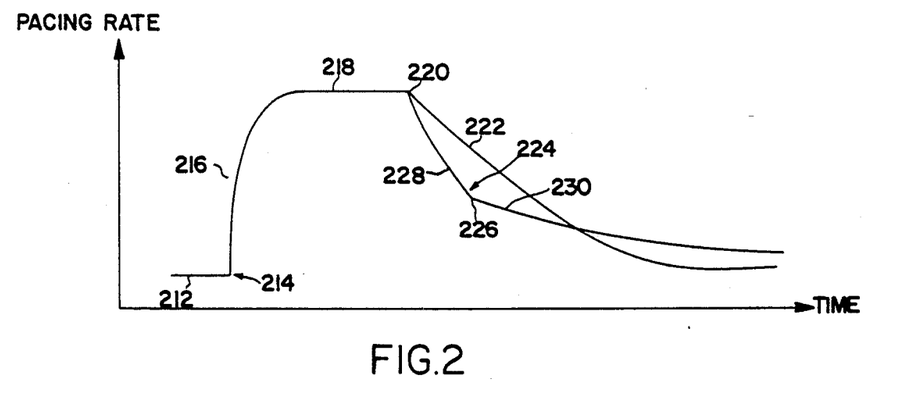
FIG. 2 is a graph illustrating the behavior of the pacemaker employing the present invention in comparison to the behavior of a conventional pacemaker.

The distinction between the behavior of a pacemaker employing the present invention and one according to the prior art is best understood by consideration of FIG. 2. FIG. 2 illustrates a pacing rate curve in a conventional activity sensing rate responsive pacemaker as compared to a normal heart decay curve. The vertical axis represents the pacing rate in pulses per minute (ppm), and the horizontal axis represents time in seconds.

In this FIG. 2, the patient is initially at rest, as indicated by the line 212, and the pacemaker is pacing at a predetermined lower rate. The deflection point 214 indicates that the patient has started to increase his or her activity level, and the attach or acceleration curve 216 shows the pacemaker responding to such increased activity level.

When the attach curve reaches a plateau 218, the pacing rate generally stabilizes at an activity determined rate or an upper rate for the duration of the exercise or physical activity. A deflection point 220 indicates that the patient's activity level has ceased or has been reduced substantially, and that the pacemaker is now ready to decelerate the pacing rate.

Two decay or deceleration curves 222 and 224 descend from the deflection point 220 and indicate a decrease in the patient's activity level. In the absence of intervening heightened activities, these two curves 222 and 224 tend to approach a predetermined pacing rate, such as the lower rate.

The decay curve 222 represents the deceleration curve in a conventional pacemaker, as exemplified in U.S. Pat. No. 4,722,342 issued to Amundson. The decay curve 224 on the other hand represents the heart's normal deceleration rate, as illustrated in a textbook by Myrvin H. Ellestad, M. D., entitled "Stress Testing Principles and Practice", pages 489-492.

It is apparent that the curves 222 and 224 do not match completely in that conventional pacemakers pace at an elevated rate, i.e. curve 222, with respect to the typical human response, i.e. curve 228, and thereafter return to the resting or lower rate sooner than the typical human response 230. This elevated pacing rate in conventional pacemakers may cause a sensation of the heart rate "racing" or beating too fast at the end of activity, perhaps even provoking a syncopal episode. Additionally, conventional pacemakers may pace too slowly for several minutes after the end of activity.

The curve 224 comprises two decay portions, an initial portion 228 and a latent portion 230, each decaying at a different time constant. As will be further explained in more details with respect to FIGS. 3 and 4, the selection of the switch point 226 and the time constants of the initial and latent decay portions 228 and 230 is an important part of the invention.

The following definition of terms used herein will assist in a better understanding of the present invention:

Achievement Criterion—A value supplied by the clinician which sets an attainment threshold for the Pacing Rate. This threshold comprises a rate component (Achievement Rate) and a time component (Achievement Duraton). The Achievement Rate is a programmable percentage of the difference between the Lower Rate (LR) and the Upper Rate (UR). The Achievement Duration is a minimum time interval over which the Sensor Pacing Rate must exceed the Achievement Rate. With rate response, the allowed programmable values for the Achievement Criterion range from 70 ppm to 175 ppm at 1 ppm intervals, and the Achievement Duration in this embodiment is fixed at a four-second interval.

Activity Count—A measure of the output of the activity sensor over a predetermined interval of time. In the preferred embodiment, each event in which the amplitude of the output exceeds a predetermined Activity Threshold for a two-second period is counted and retained. The Activity Count is updated every two-second cycle, and its aggregate value comprising the count value accumulated at the end of 3 two-second cycles (i.e., after 6 seconds) is used to calculate the sensor Target Rate for activity.

Activity Rate Response Gain—A setting which corresponds to the slope of the function correlating the activity-based sensor Target Rate of the Activity Count value which corresponds to the activity sensor output. The setting for Activity Rate Response Gain, sometimes alternately referred to as the "activity sensor gain", corresponds to a particular rate response curve (RR). With rate response, the allowed programmable values for the Activity Rate Response Gain range from 1 and 10 at setting intervals of 1.

Activity Response Time Acceleration Constant—A value which restricts the rate at which the activity-based sensor Pacing Rate can increase, such that an activity "attack" curve provides for a more gradual and physiologically appropriate change in pacing rate. In the preferred embodiment, these time values represent the time required to reach 90% of the difference between a first steady-state activity-driven pacing period (constant activity signal input for at least a six-second interval) and a second, shorter, steady-state, activity-driven pacing period when a step increase in activity level occurs. With rate response, the allowed programmable values for the Activity Response Time Acceleration Constant are selected from those of 0.25 minutes, 0.5 minutes, or 1.2 minutes.

Activity Response Time Deceleration Constant—A value which restricts the rate at which the activity-based sensor Pacing Rate can decrease, such that an activity "decay" curve provides for a more gradual and physiologically appropriate change in pacing rate. In the preferred embodiment, these time values represent the time required to reach 90% of the difference between a first steady-state activity-driven pacing period (constant activity signal input for at least a six-second interval) and a second, longer, steady-state, activity-driven pacing period when a step decrease in activity level occurs. With rate response, the allowed programmable values for the Activity Response Time Deceleration Constant are selected from those of 2.5 minutes, 5 minutes, or 10 minutes.

Activity Threshold—A minimum value which the amplitude of the activity sensor output must exceed to serve as input to the rate determination algorithm. The higher the threshold, the greater the amplitude necessary to become an event counted in the Activity Count. With rate response, the allowed programmable values for the Activity Threshold range from LOW, MEDIUM LOW, MEDIUM, MEDIUM HIGH, and HIGH.

Lower Rate (LR)—A value supplied by the clinician which establishes a lower boundary on the pacing rate. If the sensor is disabled, or its sensor output is not large enough to increase rate, the lower rate is the stimulus rate. With rate response, the allowed programmable values for LR range from 40 ppm to 100 ppm at 1 ppm intervals.

Pacing Rate—The rate calculated by the pacemaker 100 in conjunction with the activity sensor based upon its respective Target Rate and the contribution thereto based upon its respective acceleration and deceleration function.

Target Rate—The rate calculated by the pacemaker 100 in conjunction with the activity sensor based upon programmed settings and the respective sensor output.

Upper Rate (UR)—A value supplied by the clinician which limits the maximum stimulation rate when the rate responsive mode for activity, is in effect, such that the sensor-driven pacing rate generated by pacemaker 100 does not become hemodynamically excessive. With rate response, the allowed programmable values range from 100 ppm to 175 ppm at 5 ppm intervals, provided UR must also be at least 20 ppm greater than Lower Rate (LR).

Figure 3:
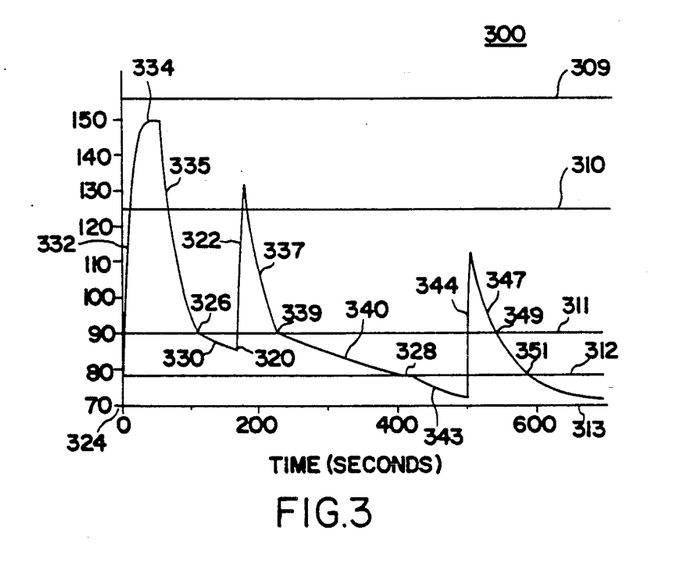
FIG. 3 is another graph further illustrating the behavior of the pacemaker employing the present invention.
Figure 4:
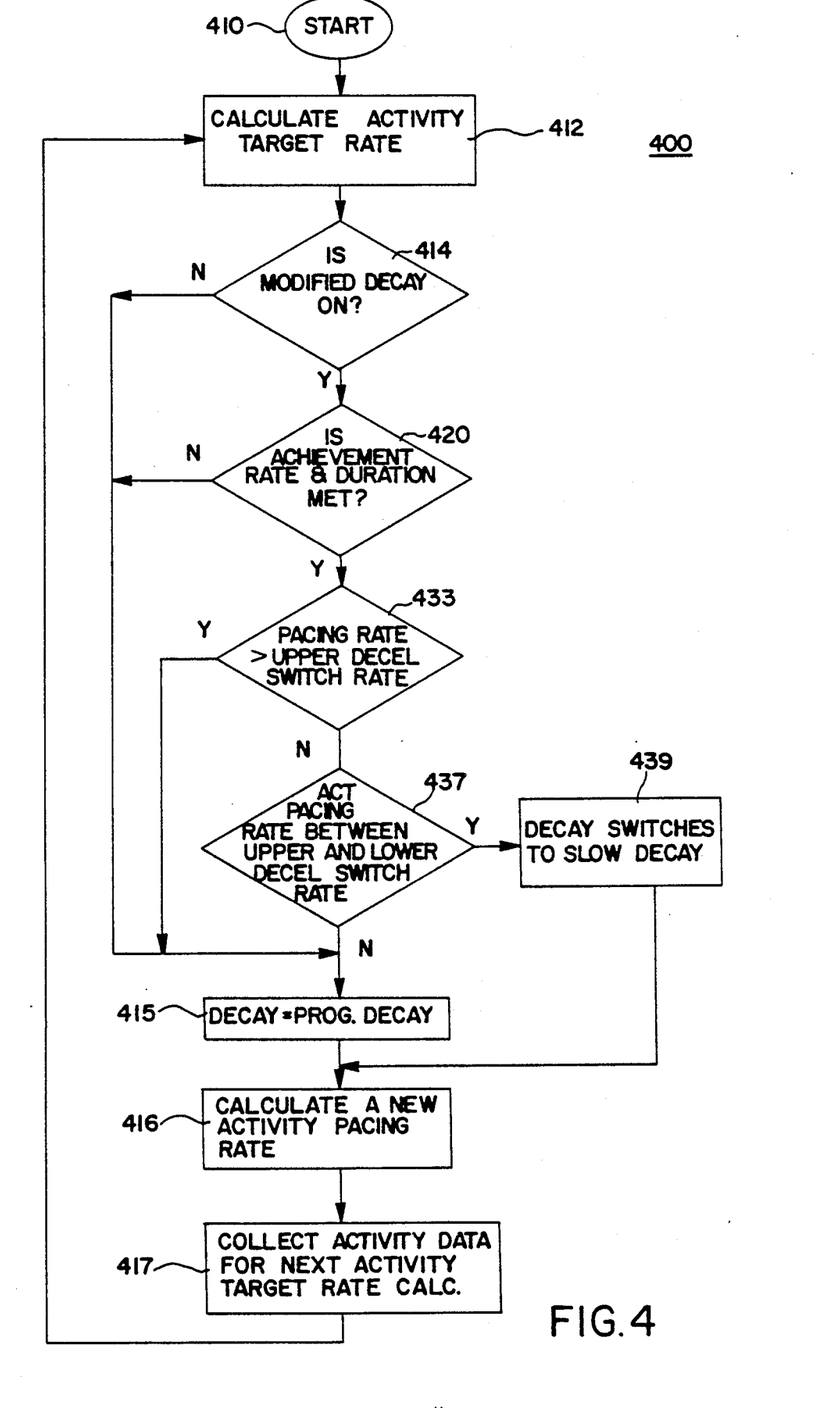
FIG. 4 is a flow chart illustrating the operation of the pacemaker according to the present invention.

The operation of the pacemaker 100 will now be described in greater details in relation to FIGS. 3 and 4. FIG. 3 illustrates an examplary activity attack and decay curve 300 indicative of the behavior of the pacemaker 100, and FIG. 4 illustrates a simplified flow chart of the software used to control the operation of the pacemaker 100 according to the present invention.

The vertical axis in FIG. 3 represents the pacing rate in pulses per minute (ppm) and the horizontal axis represents time in seconds. Five threshold levels are illustrated as horizontal lines: the upper rate 309; the achievement rate 310; the upper switch rate 311; the lower switch rate 312; and the lower rate 313.

As defined above, the upper rate 309 is a value supplied by the physician which limits the maximum stimulation rate when the activity reaches or exceeds a certain level. The pacemaker 100 is not allowed to pace above the upper rate 309. The achievement rate 310 is a value that can be set by the physician and represents a predetermined percentage of the difference between the upper rate 309 and the lower rate 313, as follows:

Achievement Rate = Lower Rate + a (Upper Rate − Lower Rate), where "a" is a percentile value which preferably ranges between 50% and 100%. The achievement rate 310 may vary from one patient to another. However, for illustration purposes, an exemplary achievement rate 310 is selected as 125 ppm.

The upper switch rate 311 is a value that can be selected by the physician and represents a predetermined percentage of the difference between the upper rate 309 and the lower rate 313, as follows:

Upper Switch Rate = Lower Rate + u (Upper Rate − Lower Rate)

where "u" is a percentile value. The upper switch rate 311 varies from one patient to another. However, the preferred range for the upper switch rate 311 is between 20% and 50%. For illustration purposes, the upper switch rate 311 is chosen as 90 ppm.

This upper switch rate 311 is an important factor in the present invention in that it determines an upper switch point 326, which is graphically represented as the intersection point between the activity curve 300 and the upper switch rate 311. This upper switch point 326 corresponds to the switch point 226 in FIG. 2.

The lower switch rate 312 is a value which is also selected by the physician, and which represents a predetermined percentage of the lower rate 313, as follows:

Lower Switch Rate=Lower Rate+10% Lower Rate.

For illustration purposes, the lower switch rate threshold 312 is chosen as 77 ppm.

The lower switch rate 312 is also an important factor in the present invention in that it determines a lower switch point 328, which is graphically represented as the intersection point between the activity decay curve 300 and the lower switch rate threshold 312.

The lower rate 313 is a value supplied by the physician which limits the minimum stimulation rate when the activity decreases to or is below a certain level. The pacemaker 100 is not allowed to pace below the lower rate 313. For illustration purposes, the lower rate 313 is chosen as 70 ppm. While the above upper rate 309, achievement rate 310, upper switch rate 311, lower switch rate 312 can be individually selected, their values can be set to default values to simplify programming procedures.

The operation of the pacemaker 100 will now be described in relation to the activity attack and decay curve 300 in FIG. 3. While the operation of the pacemaker 100 will be described in relation to a flow chart, it should be understood that the same or a similar operation can be accomplished using conventional hardware and integrated circuit technology. The initial point 324 indicates that the patient is in a resting position and that the pacemaker 100 is pacing at the lower rate 313. When the patient is stressed by exercise, the pacemaker 100 responds by increasing the pacing rate, as illustrated by the attack curve 332, until it reaches a maximum pacing rate or plateau 334, at which time, the pacing rate stabilizes for the duration of the stress. The pacing rate 334 may be limited by the upper rate 309.

If the patient maintains a heightened exercise level, and the pacemaker 100 has paced above the achievement rate 310 for a predetermined interval of time, such as 4 seconds or longer, then the pacemaker 100 automatically triggers the inventive modified decay feature, whereby the decay curve 335 is deflected at the upper and lower switch points 326 and 328, as it reaches the upper switch rate threshold 311 and the lower switch rate threshold 312 respectively. It should be understood that the waiting interval of 4 seconds could be varied for each patient, depending on age, gender and activities which the patient engages into. Nonetheless, the 4 second interval has been selected to substantially minimize false triggering by artifacts.

Thus, upon decrease of the activity level, the pacemaker 100 is allowed to pace at a decreasing rate, with a selectable decay time constant such as 45 seconds. However, once the pacing rate reaches the upper switch rate threshold 311, the decay time constant is increased in order to slow the drop in the patient's pacing rate. This modified decay feature simulates the heart's normal behavior under the circumstances, and causes the pacemaker 100 to respond optimally to the individual patient's cardiovascular needs.

The modified decay curve 330 generally corresponds to the latent decay portion 230 in FIG. 2. If, prior to reaching the lower switch rate threshold 312 the patient resumes a sudden heightened stress or exercise level, then, as indicated by the deflection point 320, the pacing rate increase correspondingly, as indicated by the attack curve 322. It should be noted that, at this stage, since the modified decay curve 330 has not reached the lower switch rate threshold 312, the modified decay feature is still enabled, and has not been turned off. The modified decay feature will be triggered off when the pacing rate drops below the lower switch rate threshold 312, along the curve 343, at which time, the modified decay feature will not be enabled until the achievement criteria have been met once again.

Therefore, as the pacing rate decay curve 337 reaches the upper switch rate threshold 311, a corresponding switch point 339 causes a change in the deceleration time constant. In this manner, the pacing rate is allowed to decay along the decay curve 337 at the time constant of 45 seconds, and upon reaching the upper switch point 339, the pacing rate follows the modified decay curve 340.

The decay time constant of the modified decay curves 330 and 340 are substantially similar, and can be selected from a range of 90 to 180 seconds, with a preferred setting of 180 seconds. It should however be understood to one skilled in the art after reviewing the present disclosure that the decay curves 330 and 340 can have different time constants, depending on the desired behavior of the pacemaker 100.

Thus, in this particular example, since the attack curve has reached and exceeded the achievement rate threshold 310, it might be desirable to set the time constant of the decay curve 340 at a value intermediate between the decay time constant of the curve 335, i.e. 45 seconds, and the modified time constant of the decay curve 330, i.e. 180 second. By analogy, the decay time constant of the curve 337 could also be selected to differ from the conventional decay time constant of the curve 335, i.e. 45 seconds.

As the curve 340 reaches the lower switch rate threshold 312, its decay time constant changes to a faster time constant 343, similar to the conventional time constant of 45 seconds. A different time constant can be selected.

Furthermore, in the preferred embodiment, upon reaching the lower switch point 328, the modified decay achievement criterion is met, such that, as long as the patient's exercise levels do not cause the pacing rate to reach or exceed the achievement rate 310 for a predetermined length of time, then the pacing rate is allowed to decay at a nominal 45 seconds time constant.

This feature is illustrated by the attack curve 344 which falls short of reaching the achievement rate threshold 310, and the decay curve 347 is followed, even though the pacing rate decays below the upper switch rate 311 and the lower switch rate 312. Hence, as illustrated, the curve 347 is allowed to decay with a single non interrupted time constant, since it is presumed that under such circumstances the patient does not require additional time to recoup from the increased sudden stress. Therefore, no deflection is effected at the intersection points 349 and 351.

It should also be understood that the pacemaker 100 can be programmed so that the intersection points 349 and 341 can become switch points similar to the upper and lower switch points 339 and 328. In the alternative, the pacemaker 100 can be programmed to cause the curve 347 to decay at a time constant different from that of the decay curve 335. Such variations are anticipated by the present description, and, for brevity purposes, they will not be characterized in greater details.

Furthermore, it should also be understood to one skilled in the art that one or more additional upper and lower switch levels can be added between the achievement rate threshold 310 and the upper switch rate threshold 311, as well as between the upper switch rate 311 and the lower rate 313, in order to generate a more gradual deflection of the overall decay curve.

Turning now to FIG. 4, the operation of the pacemaker 100 will now be described in greater detail in connection with the flow chart 400. The software program and/or hardware starts at 410, and then determines, at 412, the new target rate, according to the following equation:

$$TR = \frac{(\text{Activity Count} + D)}{C} * (32768 * 60/328)$$

Figure 6:
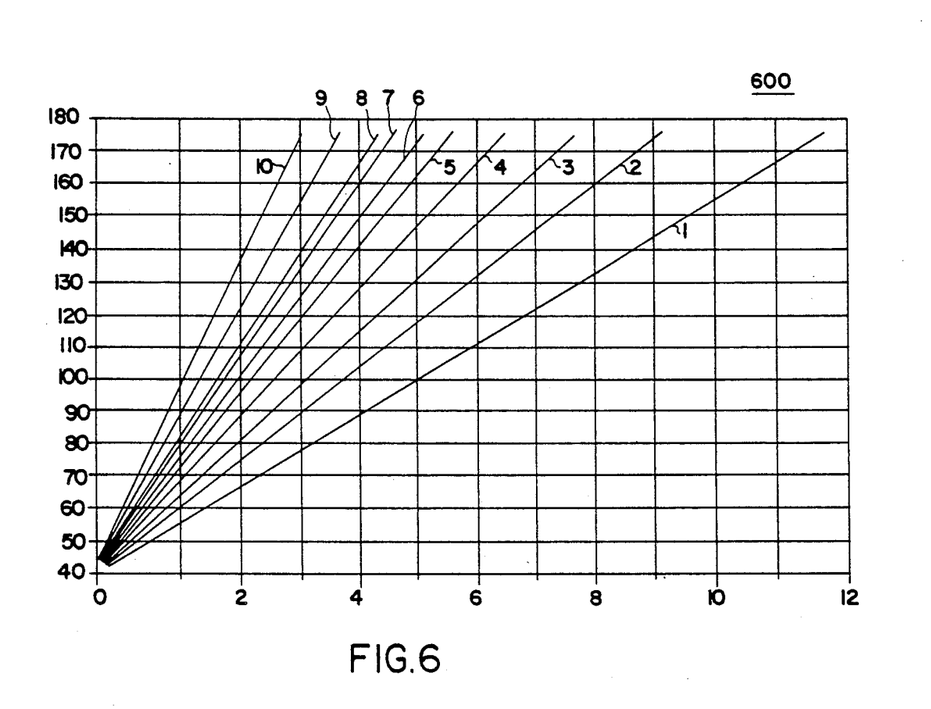
FIG. 6 is a graph of various rate response curves used in the pacemaker of the present invention.

In the above equation, TR is the target rate calculated in response to the activity sensor and C and D are programmable variables that generate the shape of the rate response curves per FIG. 6.

The values of C and D, are generated by the pacemaker 100 or by an external programmer (not shown) as a function of the selected upper rate, selected lower rate and rate response setting and are programmed into the memory or storage register of the pacemaker 100 using conventional programming techniques. The pacemaker 100 includes an arithmetic logic unit capable of making the necessary calculations and controlling the rate of the pacemaker 100 based upon the calculated target rate TR.

Each time the physician alters the selected upper rate, lower rate, or rate response settings, the programmer generates a new set of C-term, D-term, switch rates and achievement rate values, and loads them into the memory or program registers of the pacemaker 100, so that the arithmetic logic unit may calculate the target rate thereafter based upon the updated values. Regardless of which of the selected parameters has changed, the resulting function relating the pacing rate to the sensor output will take the same basic form, extending from the lower rate at a minimal sensor output to the upper rate at an achievable sensor output, with a sensor output required to achieve the upper rate decreasing as the rate response setting is increased.

A more detailed description of the above calculations can be found in the co-pending application, Ser. No. 455,717, entitled "METHOD AND APPARATUS FOR IMPLEMENTING ACTIVITY SENSING IN A PULSE GENERATOR", filed on Dec. 22, 1989, which is incorporated herein by reference. Thus, as indicated at block 412, the pacemaker 100 periodically calculates the activity target rate TR, at a two-second interval, along the curve 300 of FIG. 3.

Next, the software determines at 414, whether the modified decay feature has been activated or programmed via a programmer such as Medtronic Model 9760. If the modified decay feature has not been activated, then, the software sets, at 415, the decay rate to be equal to the programmed decay rate, i.e., in this example, 45 seconds time constant.

The pacemaker then calculates the next activty pacing rate at 416, and saves the activity related data, at 417, for use in calculating the new activity target rate at 412. The above routine is repeated until the modified decay feature is activated.

If the modified decay feature has been enabled at 414, then, as indicated by block 420, the software determines whether the achievement criterion has been met, i.e. whether the pacing rate is greater than or equal to the achievement rate 310, for a period of 4 seconds or longer. If the achievement criterion has not been met, then the software sets, at 415, the decay rate to be equal to the programmed decay rate, calculates the activity pacing rate at 416, saves the activity data at 417, and then calculates the new activity target rate at 412.

If on the other hand, the achievement criterion has been met, then, as illustrated by block 433, the software determines whether the current pacing rate is greater than the upper switch rate threshold 311. If it is, then, once again, the software sets, at 415, the decay rate to be equal to the programmed decay rate, calculates the activity pacing rate at 416, saves the activity data at 417, and calculates the new activity target rate at 412.

If the pacing rate is less or equal to the upper switch rate 311, then the software determines, at 437, whether the pacing rate is between the upper switch rate 311 and the lower switch rate 312. If it is, then, as indicated by block 439, the software changes the decay rate to the modified or slower decay rate, as illustrated by the decay curves 330 and 340 in FIG. 3. The activity pacing rate is calculated at 416, the activity data is then saved at 417, and a new activity target rate is calculated at 412.

If the pacing rate is less than the lower switch rate 312 then as indicated by block 415, the software changes the decay rate to the programmed value.

Figure 5:
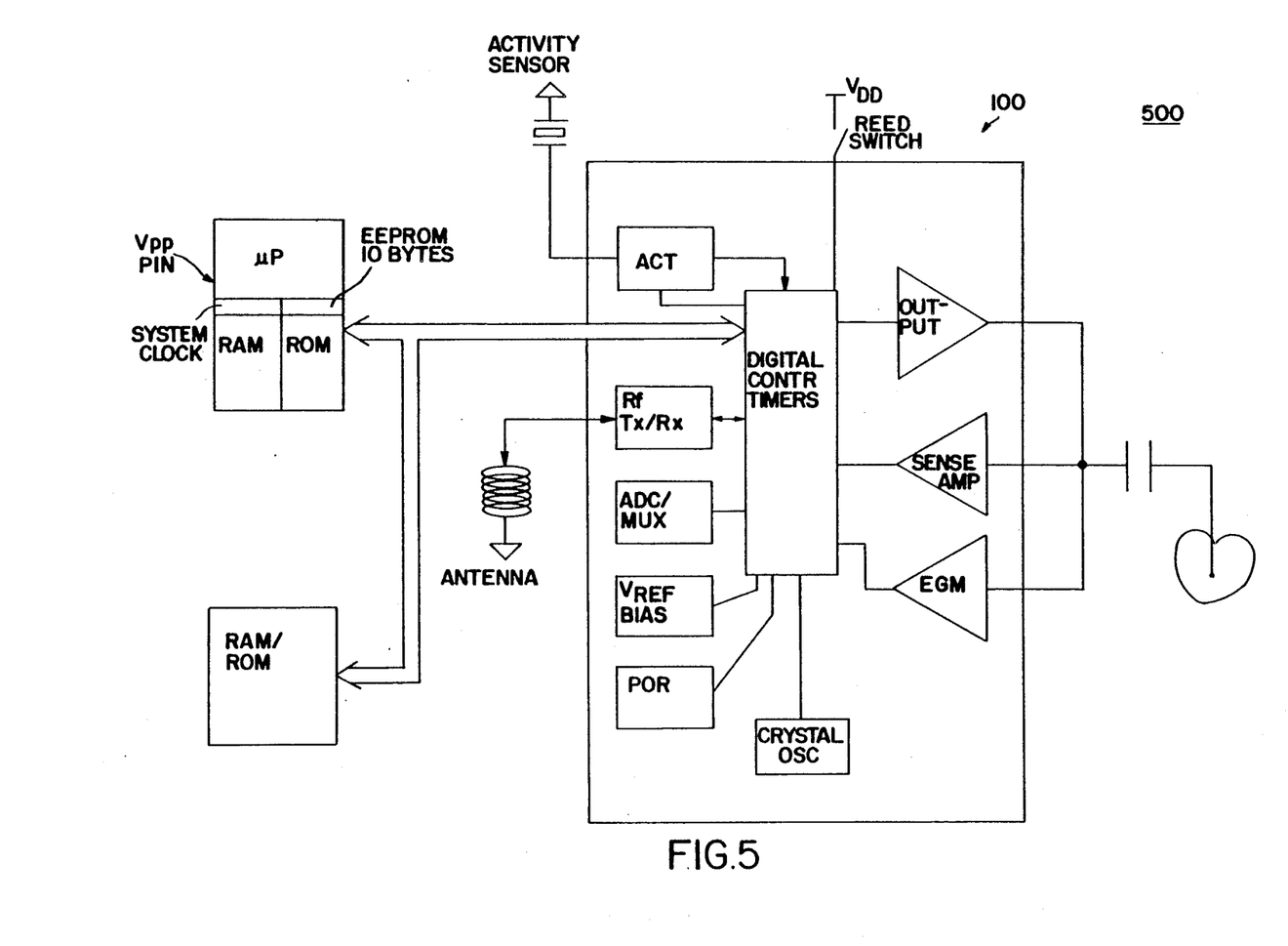
FIG. 5 is a block diagram illustration of a simplified cricuit for the pacemaker according to the present invention.

Turning now to FIG. 5, there is illustrated a block circuit diagram 500 of the pacemaker 100 utilizing a microprocessor with on-board and off-board RAM/ROM memory and an activity sensor for adjusting the physiologic pacing rate as a function of the patient activity. The functional description of the circuit 500 is provided in detail in the co-pending application Ser. No. 549,568, entitled "METHOD AND APPARATUS FOR ACCESSING A NON-VOLATILE MEMORY", filed on Jul. 6, 1990, and having the same assignee as the present application, and is incorporated herein by refererence.

Turning now to FIG. 6, there is illustrated a graph 600 of ten rate response curves used in the pacemaker 100. The programmed rate response setting establishes the relationship of the pacing rate to the detected physical activity. The rate response has ten settings. The most responsive setting (10) permits the greatest incremental change in response to detected activity. The least responsive setting (1) allows the smallest incremental change in response to be detected by activity. When a change in the level of physical activity is detected, the pacing will change gradually up and down, as the case may be along the selected setting, i.e., (5). The change is affected by a combination of several parameters, such as activity threshold, rate response, upper and lower rates, and is intended to imitate the rate responsiveness of the normal heart.

The graph 600 is described in details in the co-pending application, Ser. No. 455,717, entitled "METHOD AND APPARATUS FOR IMPLEMENTING ACTIVITY SENSING IN A PULSE GENERATOR", filed on Dec. 22, 1989 and having the same assignee as the present application, and is incorporated herein by reference.

While particular embodiments of the present invention have been disclosed, it is to be understood that various different modifications are possible and are contemplated within the scope of the specification, drawings, abstract and appended claims.

What is claimed is:

1. Method for pacing along a decay curve having a decay time constant, the pacing method comprising the steps of:
   a. selecting a set of predetermined achievement criteria;
   b. selecting a first pacing switch rate threshold;
   c. determining whether said achievement criteria have been met; and
   d. if said achievement criteria have been met, then modifying the decay time constant of the decay curve from a first value to a second value, as the pacing rate drops below said first pacing switch rate threshold, such that said second value is different from said first value.

2. The method as defined in claim 1, further including the steps of:
   a. selecting a second pacing switch rate threshold lower than said first pacing switch rate threshold; and
   if said achievement criteria have been met, then modifying the decay time constant of the decay curve from the second value to a third value, as the pacing rate drops below said second pacing switch rate threshold, such that said second value is different from said third value.

3. The method as defined in claim 2, wherein said second value of the time constant for the decay curve is longer than said first value, in order to allow a slower decay of the pacing rate.

4. The method as defined in claim 3, wherein said third value of the 5 time constant for the decay curve is substantially equal to said first value.

5. The method as defined in claim 1, further including the step of keeping the time constant of the decay curve unchanged if said achievement criteria have not been met.

6. The method as defined in claim 1, wherein said achievement criteria includes an achievement rate and an achievement time interval; wherein said achievement rate is a programmable percentage of the difference between a Lower Rate (LR) and an Upper Rate (UR); wherein said Lower Rate and Upper Rate are the lower and upper pacing rates respectively; and wherein the achievement time interval is a minimum time interval over which the pacing rate exceeds said achievement rate.

7. The method as defined in claim 6 wherein said achievement time interval is about 4 seconds.

8. The method as defined in claim 6, wherein said achievement rate is calculated as follows:

$$\text{Achievement Rate} = \text{Lower Rate} + a\ (\text{Upper Rate} - \text{Lower Rate}),$$

where "a" is a percentile value which ranges between 50% and 100%, and the Lower Rate and the Upper Rate are the lower and upper pacing rates respectively.

9. The method as defined in claim 6, wherein said achievement rate is 125 pulses per minute.

10. The method as defined in claim 2, wherein said first pacing switch rate threshold is calculated as follows:

$$\text{First Pacing Switch Rate} = \text{Lower Rate} + u\ (\text{Upper Rate} - \text{Lower Rate})$$

where "u" is a percentile value which ranges between 20% and 50%, and where the Lower Rate and the Upper Rate are the lower and upper pacing rates respectively.

11. The method as defined in claim 10, wherein said first pacing switch rate is about 90 pulses per minute.

12. The method as defined in claim 10, wherein said second pacing switch rate threshold is calculated as follows:

$$\text{Second Pacing Switch Rate} = \text{Lower Rate} + 10\%\ \text{Lower Rate}.$$

13. The method as defined in claim 12, wherein said second pacing switch rate is about 77 pulses per minute.

14. The method as defined in claim 1, further including the steps of:
   a. using an activity sensor to sense cardiac events, and to generate an output indicative of the amplitude of the sensed cardiac events; and
   b. calculating a target rate, wherein said step of calculating said target rate, is performed according to the following equation:

$$TR = \frac{(\text{Activity Count} + D)}{C} * (32768 * 60/328),$$

where C and D are selectively programmable values, and where said Activity Count is a measure of said activity sensor output over a predetermined interval of time.

15. A cardiac pacemaker of the type having a pulse generator for generating stimulus pulses, comprising: means for pacing along a decay curve having a decay time constant, comprising:
   i) means for selecting a set of predetermined achievement criterion;
   ii) means for selecting a first pacing switch rate threshold;
   iii) means for determining whether said achievement criterion has been met; and
   iv) means for modifying the decay time constant of the decay curve from a first value to a second value, as the pacing rate drops below said first pacing switch rate threshold, such that said second value is different from said first value, if said achievement criterion has been met.

16. The cardiac pacemaker as defined in claim 15, wherein said pacing means further includes:
   a. means for selecting a second pacing switch rate threshold lower than said first pacing switch rate threshold; and
   b. means for modifying the decay time constant of the decay curve from the second value to a third value, if said achievement criteria have been met, as the pacing rate drops below said second pacing switch rate threshold, such that said second value is different from said third value.

* * * * *